(12) United States Patent
Daiju

(10) Patent No.: US 7,922,677 B2
(45) Date of Patent: Apr. 12, 2011

(54) ROTARY JOINT OF ARTICULATION PROSTHETIC IMPLEMENT HAVING ROTATING LOAD SETTING MEANS, ARTICULATION PROSTHETIC IMPLEMENT USING THE ROTARY JOINT AND METHOD OF MAKING ARTICULATION PROSTHETIC IMPLEMENT

(75) Inventor: Satoru Daiju, Kouchi (JP)

(73) Assignee: Hokushinkai Medical Corp., Hei, Himi, Saijo-shi, Ehime (JP)

( * ) Notice: Subject to any disclaimer, the term of this patent is extended or adjusted under 35 U.S.C. 154(b) by 203 days.

(21) Appl. No.: 12/232,413

(22) Filed: Sep. 17, 2008

(65) Prior Publication Data

US 2009/0030357 A1  Jan. 29, 2009

Related U.S. Application Data

(62) Division of application No. 11/007,201, filed on Dec. 9, 2004, now Pat. No. 7,438,698.

(30) Foreign Application Priority Data

Feb. 4, 2004  (JP) ................................. 2004-027715

(51) Int. Cl.
*A61F 5/00*  (2006.01)
(52) U.S. Cl. .................. 602/5; 602/16; 602/20; 602/23; 602/27
(58) Field of Classification Search .................... 623/39, 623/41–45; 602/5, 16, 20–23, 26–29
See application file for complete search history.

(56) References Cited

U.S. PATENT DOCUMENTS

| 5,549,712 | A | * | 8/1996 | Gammer et al. | ................ | 623/60 |
| 6,280,404 | B1 | * | 8/2001 | Morinaka et al. | ................ | 602/16 |
| 7,438,698 | B2 | * | 10/2008 | Daiju | .............................. | 602/16 |

FOREIGN PATENT DOCUMENTS

WO  WO 02/39934 A1  5/2002

* cited by examiner

*Primary Examiner* — Kim M Lewis
(74) *Attorney, Agent, or Firm* — Bacon & Thomas, PLLC

(57) ABSTRACT

A method of manufacturing an articulation prosthetic implement includes the steps of previously manufacturing a onway clutch covered and fitted with a metal bush, the metal bush covered and fitted with a synthetic resin bush, and the synthetic resin bush covered and fitted with a brake bush; covering and fitting a rotary shaft of an outer member with flanges at either end, having a rotary shaft at the inner side and an annular depression around the rotary shaft, with the oneway clutch having the three bushes; fitting a cylindrical projection of an inner member having flanges at either end into the annular depression of the outer member located outside the brake bush; screwing or bolting a stopper for controlling the range of rotary shaft rotation to an inner projection of the rotary shaft; fitting one articulation protecting member of the articulation prosthetic implement to the flange of the inner member from the surface side of the inner member; and fitting the other articulation protecting member of the articulation prosthetic implement to the flange of the outer member form the surface side of the outer member.

1 Claim, 19 Drawing Sheets

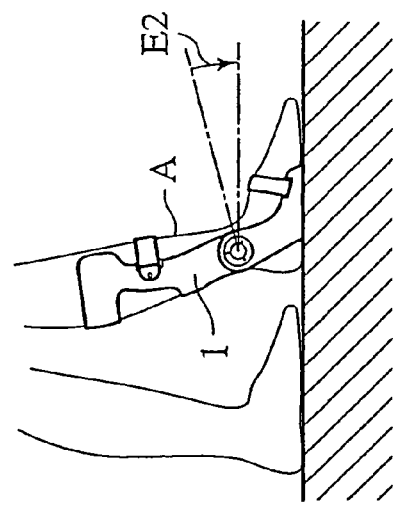
FIG. 8A
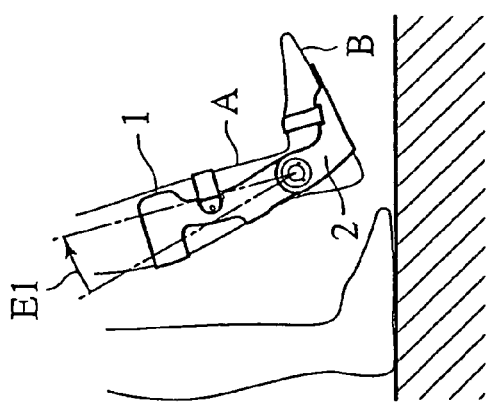
FIG. 8B
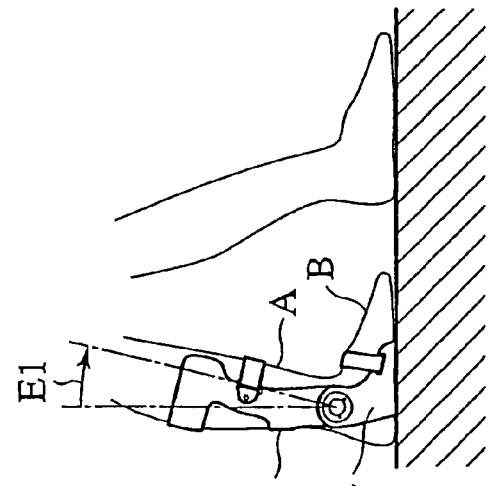
FIG. 8C
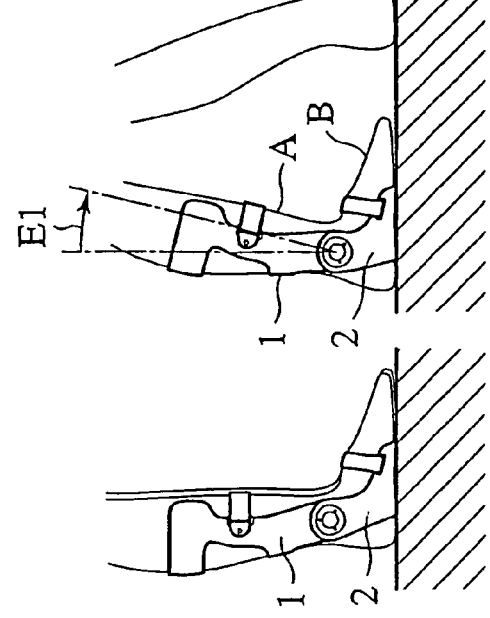
FIG. 8D FLAT ROAD

UPWARD SLOPE

DOWNWARD SLOPE

ROTARY JOINT OF ARTICULATION PROSTHETIC IMPLEMENT HAVING ROTATING LOAD SETTING MEANS, ARTICULATION PROSTHETIC IMPLEMENT USING THE ROTARY JOINT AND METHOD OF MAKING ARTICULATION PROSTHETIC IMPLEMENT

CROSS-REFERENCE TO RELATED APPLICATION

This application is a Divisional of U.S. patent application Ser. No. 11/007,201, which was filed on Dec. 9, 2004.

BACKGROUND OF THE INVENTION

The present invention relates to the improvement of a rotary joint of an articulation prosthetic implement having a rotating load setting means, an articulation prosthetic implement using the improved rotary joint, and a method of making (assembling) the articulation prosthetic implement. The present invention is effective as an articulation prosthetic implement for rectification of clubfoot in particular. That is, it can be effectively used for an articulation prosthetic implement configured in that one articulation protecting member out of vertically adjoining articulation protecting members is rotatable against the other articulation protecting member about the axial center in a direction vertical to the adjoining direction.

Clubfoot (talipes equinovarus) is a foot in a state such that the foot turns inward causing the sole to be faced inward, making it unable to control the ankle, and the toe tip side (hereinafter called foot tip) droops downward, and the person is liable to stumble as the foot tip touches the ground in walking, thereby causing hindrance to the walking function.

And, for preventing such stumbling during walking, generally employed is a method that the foot tip is rectified upward in order to prevent the foot tip from drooping downward, and as an articulation prosthetic implement (lower limb implement) to achieve the purpose, various types have been conventionally proposed. As shown in FIG. 7B, a normal state is such that the foot is positioned (shown by solid line) in parallel to the horizontal direction perpendicular to the leg being parallel to the vertical direction, and in that condition, when the foot is moved upward about the ankle bone as shown by imaginary line (chain double-dashed line), it is called back flexion, and when moved downward, it is called bottom flexion.

In the case of a conventional articulation prosthetic implement, for example, it is configured in that a lower articulation protecting member is rotatably connected to a vertically adjoining upper articulation protecting member, and the lower articulation protecting member is rotatable to the back flexion side from the normal state only in a range of a predetermined angle (e.g. 45 deg), and thereby, it is free from bottom flexion from the normal state while being able to make back flexion.

When walking on a flat road by using a conventional articulation prosthetic implement, the normal leg is moved a step forward, and subsequently, the leg on the articulation prosthetic implement is a little inclined forward [see FIG. 8B] just before the leg on the articulation prosthetic implement is moved upward, and as a result, the lower articulation protecting member turning to the back flexion side returns to the normal state due to the foot weight simultaneously when the foot is moved upward, and thereby, it is possible to lessen a chance of stumbling as compared with the case of a foot tip drooping downward.

However, when walking on a downward slope, it is necessary to rotate the articulation protecting member at the foot side (lower side) to the bottom flexion side against the articulation protecting member at the leg side (upper side), but in the above configuration, it is unable to make bottom flexion and the walking is unstable in a bending forward condition, and it is sometimes difficult to make a nearly natural walk. Also, as the foot is placed on the ground when walking on an upward slope, the lower articulation protecting member which supports the foot is able to make back flexion, but when the foot being in a state of bottom flexion is moved up, the lower articulation protecting member returns to the horizontal position due to the foot weight, and it sometimes causes the foot tip to touch the downward slope. By changing the configuration to the one having a rotating angle such that bottom flexion can be made on a downward slope, it is able to walk on a downward slope, but when moving from a downward slope onto a flat road or an upward slope, the configuration is not enough to enable nearly normal walking, and it is very difficult to handle.

In order to solve the above problem, as a prosthetic implement that enables nearly natural walking without limitations on bottom flexion and back flexion, in body prosthetic implements having such a configuration that one body protecting member out of vertically adjoining body protecting members is freely rotatable against the other body protecting member, well-known is the one provided with a rotating load setting means for setting the rotating load to one rotating direction of the freely rotatable body protecting member greater than the rotating load to the other rotating direction (for example, refer to the patent document 1).

[Patent Document 1] International Publication No. 02/39934 Pamphlet (PCT WO02/39934 A1)

However, the rotary section of the prosthetic implement mentioned in the patent document 1 has a cross-section as shown in FIG. 19. That is, circular openings 80K are formed at the lower right and left sides of lower thigh rear plate 80, and inner cylindrical member 86 made of metal (it is preferable to use the one made of synthetic resin or the like if any provided that it has rigidity) which has flange 86A is inserted into one end of the opening 80K from inside, and the flange 86A and lower thigh rear plate 80 are fixed with a plurality of screws B80. Also, circular opening 82K is formed at the upper end of foot bottom plate 82, and outer member 87 made of metal (it is preferable to use the one made of synthetic resin or the like if any provided that it has rigidity) which is externally circular having flange 87A and annular-circular depression 87B is inserted into the opening 82K from inside, and the flange 87A and foot bottom plate 82 are fixed with a plurality of screws B82. And, annular one-way bearing 88 as a rotating load setting means is externally fitted onto circular rotary shaft 87C formed at the center of outer member 87, and the inner cylindrical member 86 is fitted into the remaining space of depression 87B whose space is partially occupied by the one-way bearing 88 externally fitted thereon. Also, stopper 89 which engages projection 87D formed at one end in the axial direction of rotary shaft 87C is fixed on the projection 87D with one screw B83.

Thus, at the rotating section of the conventional prosthetic implement shown in FIG. 19, lower thigh rear plate 80 must be fixed on flange 86A at each end of inner cylindrical member 86 by using screws B80, and it is difficult to perform the torque test of rotary joint (the configuration of FIG. 19 except lower thigh rear plate 80 and foot bottom plate 82).

Also, the rotating load setting means in FIG. 19 comprises outer member 87 internally having a circular depression, inner cylindrical member 86 having a circular projection which engages the outer member, circular one-way bearing 88 inserted into the portion held between the projection and depression of the two members, stopper 89 which engages a disk piece provided at the one-way bearing and the inner cylindrical member, and screw B53 which goes through the screw hole provided in the stopper and the screw hole provided in the outer member. One-way bearing 88 rotates in one direction, but it does not rotate at all in the other direction (opposite direction) even with a force applied, and regarding the configuration of the rotating load setting means, the description is not clear enough to enable the execution of the actual work.

OBJECT AND SUMMARY OF THE INVENTION

The problem to be solved is that it is necessary to build in a lower thigh rear plate during assembly of a rotary joint, and the rotary joint cannot be assembled and completed beforehand in the form of a single unit.

In the present invention, the lower thigh rear plate and foot bottom plate of the articulation prosthetic implement can be assembled after completion of the rotary joint assembly, and the rotary joint can be easily subjected to the torque test in the form of a single unit, thereby enabling the stabilization of load, and this is the most significant characteristic of the present invention.

The articulation prosthetic implement having a rotating load setting means of the present invention comprises an outer member (outer housing) with flanges at either end, having an inner rotary shaft and an annular depression (groove) around the rotary shaft, a one-way clutch for externally engaging the rotary shaft, a metal bush for externally engaging the one-way clutch, a synthetic resin bush for externally engaging the metal bush, a brake bush for externally engaging the synthetic resin bush, and a cylindrical projection which is fitted in the annular depression of the outer member located outside the brake bush, wherein the rotary joint having a rotating load setting means is configured with an inner member (inner housing) having flanges at either end and a stopper mechanism for controlling the range of the rotary shaft rotation which is installed at the inner projection of the rotary shaft, and one articulation protecting member of the articulation prosthetic implement is fitted to the flange of the inner member from the surface side (foot touching side) of the inner member, and the other articulation protecting member of the articulation prosthetic implement is fitted to the flange of the outer member from the surface side (outside) of the outer member.

In this rotary joint, the stopper of the stopper mechanism has a projection, and the projection is fitted in a long groove provided at the disk piece of the inner member. Also, the brake bush is made of silicone resin.

Also, the articulation prosthetic implement of the present invention is configured in that one articulation protecting member is rotatably connected via a rotary joint to the other articulation protecting member adjoining vertically of the articulation, and in the articulation prosthetic implement provided with a rotary joint having a rotating load setting means for setting the rotating load to one rotating direction of the freely rotatable articulation protecting member larger than the rotating load to the other rotating direction, the rotary joint having the rotating load setting means has a rotary shaft at the inner side and an annular depression around the rotary shaft, and an outer member having flanges at either end, a one-way clutch for externally engaging the rotary shaft, a metal bush for externally engaging the one-way clutch, a synthetic resin bush for externally engaging the metal bush, a brake bush for externally engaging the synthetic resin bush, and a cylindrical projection which is fitted in the annular depression of the outer member located outside the brake bush, wherein it is configured with an inner member having flanges at either end and a stopper mechanism for controlling the range of the rotary shaft rotation which is installed at the inner projection of the rotary shaft, and one articulation protecting member of the articulation prosthetic implement is fitted to the flange of the inner member from the surface side of the inner member, and the other articulation protecting member of the articulation prosthetic implement is fitted to the flange of the outer member from the surface side of the outer member.

In this articulation prosthetic implement, the stopper of the stopper mechanism has a projection, and the projection is fitted in a long groove provided at the disk piece of the inner member. Also, the brake bush is made of silicone resin.

In these articulation prosthetic implements, the articulation protecting member comprises a foot bottom plate which partially or entirely supports the sole, and a leg protecting plate of which an upper articulation member partially or entirely protects the leg, and side-end portions where these members are adjoining are connected to each other via the rotary joint having a rotating load setting means, thereby setting up a lower limb implement.

Also, when walking by using an articulation prosthetic implement provided with a leg protecting plate and foot bottom plate, the foot bottom plate is rotated so that the bottom of the foot bottom plate is paralleled with the ground due to the load applied when the foot bottom plate touches the ground, and the rotating load is set so that the state just before moving up the foot bottom plate and leg protecting plate is maintained when the foot bottom plate is moved up.

Also, the leg protecting plate comprises a lower thigh rear plate for protecting the calf, and the heel-bone part at the rear of foot bottom plate and the Achilles' tendon part at the lower end rear of lower thigh rear plate are of open type.

And, the rotational center of the lower thigh rear plate is set to a height nearly the same as the vertical height position of hominal physiological foot joint axis. Also, an upper opening and lower opening are formed in the lower thigh rear plate. Also, the right and left front ends of the lower thigh rear plate are provided with a fixing member for fastening and fixing the lower thigh to the lower thigh rear plate, while the right and left ends of the foot bottom plate are provided with a fixing member for fastening and fixing the foot instep to the foot bottom plate.

The rotating load setting means comprises a freely rotatable one-way clutch disposed at the rotary shaft, a metal bush which covers the one-way clutch, a synthetic resin bush which covers the metal bush, and a brake bush which covers the synthetic resin bush.

Also, it comprises a foot bottom plate which partially or entirely supports the sole, a leg protecting plate which partially or entirely protects the leg, and a rotating load setting means provided at the rotary shaft of the leg protecting plate in order to maintain the state just before moving up the foot bottom plate and leg protecting plate when the foot bottom plate is moved up by rotating the foot bottom plate so that the bottom of the foot bottom plate is paralleled with the ground due to the load applied when the foot bottom plate touches the ground for walking.

As an articulation prosthetic implement, it comprises a thigh protecting member which partially or entirely covers the thigh and a lower thigh protecting member which partially or entirely covers the lower thigh, and it is possible to set up a leg implement by connecting the adjoining sides of these members via a rotary joint having a rotating load setting means.

Also, as an articulation prosthetic implement, it comprises an upper arm protecting member which partially or entirely covers the upper arm and a fore-arm protecting member which partially or entirely covers the fore-arm, and it is possible to set up an arm implement by connecting the adjoining sides of these members via a rotary joint having a rotating load setting means. Also, in the lower limb implement, it is sometimes configured in that the plantar portion is integrally disposed at the bottom of a shoe.

Also, in the method of making (assembling) the articulation prosthetic implement of the present invention, previously manufactured is the one with a one-way clutch covered and fitted with a metal bush, the metal bush covered and fitted with a synthetic resin bush, and the synthetic resin bush covered and fitted with a brake bush, wherein there are provided a rotary shaft at the inner side and an annular depression around the rotary shaft, and after covering and fitting the rotary shaft of an outer member having flanges at either end with the one-way clutch having the three bushes, the cylindrical projection of an inner member having flanges at either end is fitted in the annular depression of the outer member located outside the brake bush, and subsequently, after screwing or bolting a stopper for controlling the range of rotary shaft rotation to the inner projection of the rotary shaft, one articulation protecting member of the articulation prosthetic implement is installed on the flange of the inner member from the surface side of the inner member, and also, the other articulation protecting member of the articulation prosthetic implement is installed on the flange of the outer member from the surface side of the outer member.

BRIEF DESCRIPTION OF THE DRAWINGS

FIG. 2 includes explanatory diagrams of a sectional view showing the operation mechanism of a one-way clutch.

FIG. 6 is an explanatory diagram showing the operation of a stopper.

FIG. 7 is an explanatory diagram showing the operation of a stopper greater in width than the stopper of FIG. 6.

FIG. 8 shows a state of walking on a flat road with use of the articulation prosthetic implement in the first embodiment of the present invention. FIG. 8A shows a state of walking with the feet arranged in order. FIG. 8B shows a state of walking with the left foot moved a step forward. FIG. 8C shows a state of walking just before landing with the right foot stepped forward. FIG. 8D shows a state of walking with the right foot stepped forward and landed.

FIG. 9 shows a state of walking on an upward slope with use of the articulation prosthetic implement in the first embodiment of the present invention.

FIG. 10 shows a state of walking on a downward slope with use of the articulation prosthetic implement in the first embodiment of the present invention.

FIG. 14 shows an articulation prosthetic implement in the second embodiment of the present invention.

DETAILED DESCRIPTION OF PREFERRED EMBODIMENTS

Figure 1:
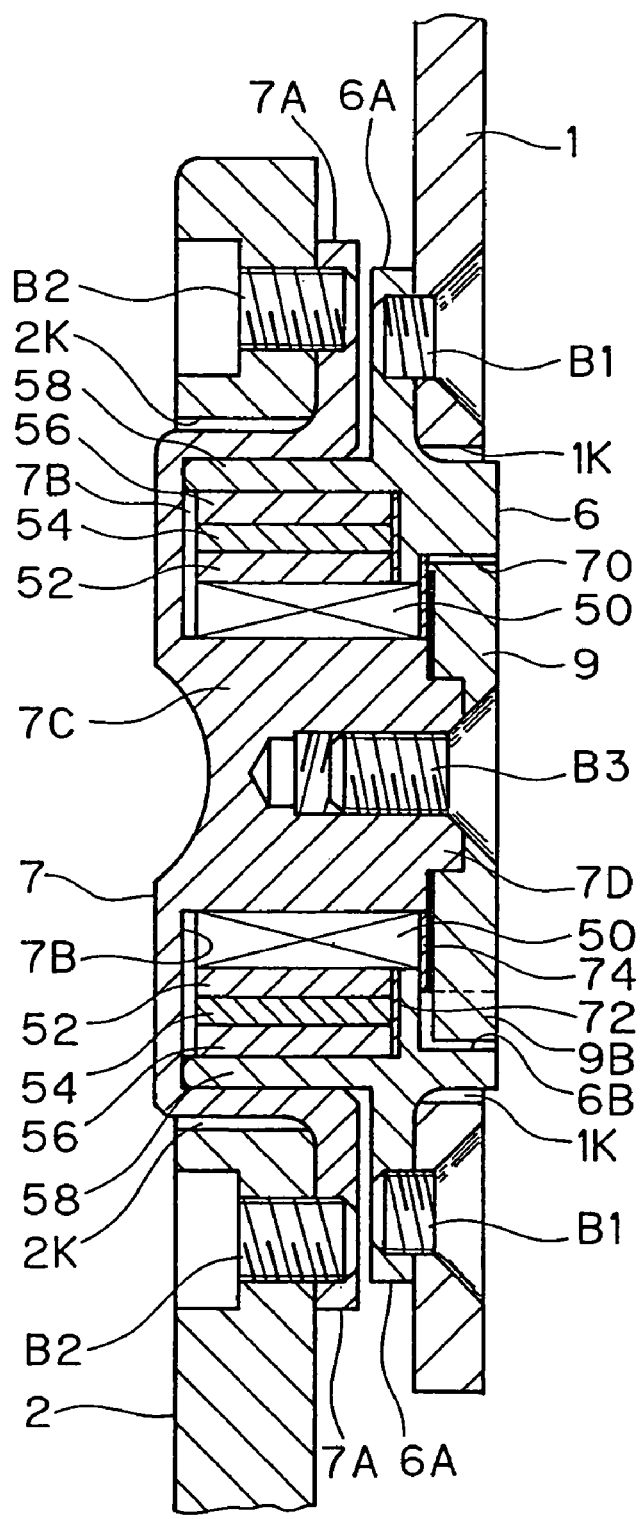
FIG. 1 is a sectional view around an articulation prosthetic implement having a rotating load setting means in the first embodiment of the present invention.

Referring now to the drawings, some of the preferred embodiments of the invention are described in detail below.

In the present invention, the purpose of making easier the torque test of a rotary joint or the like has been achieved by using such a method that the articulation protecting means is installed after completing the rotary joint assembly instead of employing a conventional method in which one articulation protecting means is installed during the assembly of a rotary joint.

The preferred embodiments of the present invention will be described in the following. The present invention is not limited by the following preferred embodiments, and it is preferable to properly change the invention.

FIG. 1 shows a section around a rotary joint of an articulation prosthetic implement having a rotating load setting means in the first embodiment of the present invention.

The rotary joint comprises outer member (outer housing) 7 with flanges 7A at either end, having rotary shaft 7C at the inner side and annular depression (groove) 7B around the rotary shaft; one-way clutch 50 for externally engaging the rotary shaft 7C; metal bush 52 for externally engaging the one-way clutch 50; synthetic resin bush 54 for externally engaging the metal bush 52; brake bush 56 for externally engaging the synthetic resin bus 54; inner member (inner housing) 6 with flanges 6A at either end, having cylindrical projection 58 which is fitted in the annular depression 7B of the outer member located outside the brake bush 56, and a stopper mechanism having stopper 9 or the like for controlling the range of rotary shaft rotation which is installed at inner projection 7D of rotary shaft 7C. The rotary joint is formed by assembling these component elements. Reference numeral B3 is a screw or bolt, numeral 70 is a circular groove (see, also, FIG. 7A), and numerals 72, 74 are spacers.

And, lower thigh rear plate 1, one articulation protecting member of the articulation prosthetic implement, is fitted to the flange 6A of inner member 6 of the rotary join assembly from the surface side (right-hand side in FIG. 1) of the inner member, and foot bottom plate 2, the other articulation protecting member of the articulation prosthetic implement, is fitted to the flange 7A of outer member 7 from the surface side (left-hand side in FIG. 1) of the outer member. Reference numerals B1, B2 are screws or bolts.

Stopper 9 of the stopper mechanism has projection 9B, and it is configured that the projection is fitted in long groove 6B provided at the disk piece of the inner member.

As metal bush 52, for example, the one made of stainless steel is used, and as synthetic resin bush 54, for example, the one made of nylon is used, and as brake bush 56, the one made of silicone resin is used. And, the rotating load can be adjusted by changing the hardness of silicone resin.

Figure 2A:
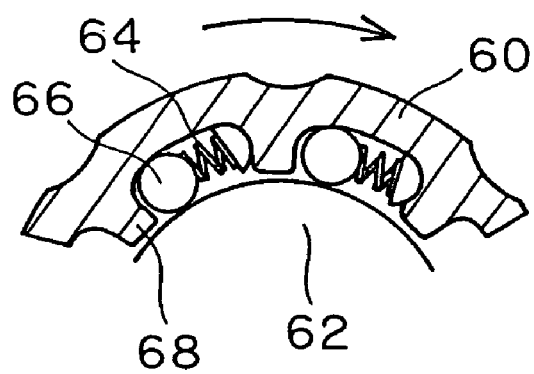
FIG. 2A shows the clutch in a state of being engaged.

FIG. 2 is an explanatory diagram of a sectional view showing the operation mechanism of one-way clutch 50. FIG. 2A shows the clutch in a state of being engaged, and FIG. 28 shows a state of the clutch in a state of being released. As shown in FIG. 2A, when outer ring 60 rotates clockwise against shaft 62, the action of spring 64 causes roller 66 to go to the engaging position of outer ring cam 68 surface, then shaft 62 is driven by the wedge effect between outer ring cam 68 surface and shaft 62.

Figure 2B:
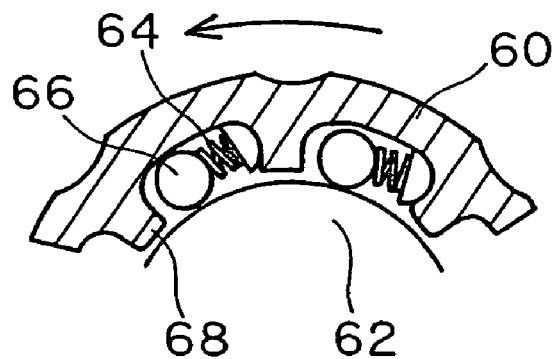
FIG. 2B shows the clutch in a state of being released.

On the other hand, as shown in FIG. 2B, when outer ring 60 turns counterclockwise against shaft 62, shaft 62 rotates clockwise in relation to outer ring 60, and roller 66 moves apart from outer ring cam 68 surface, then outer ring 60 runs idle against shaft 62. The metal bush 52, synthetic resin bush 54, and brake bush 56 are sequentially covered and fitted on outer ring 60, and it is configured in that, even when the clutch shown in FIG. 2A is in engagement, brake bush 56 may slide on cylindrical projection 58 of inner member 6.

Figure 3:
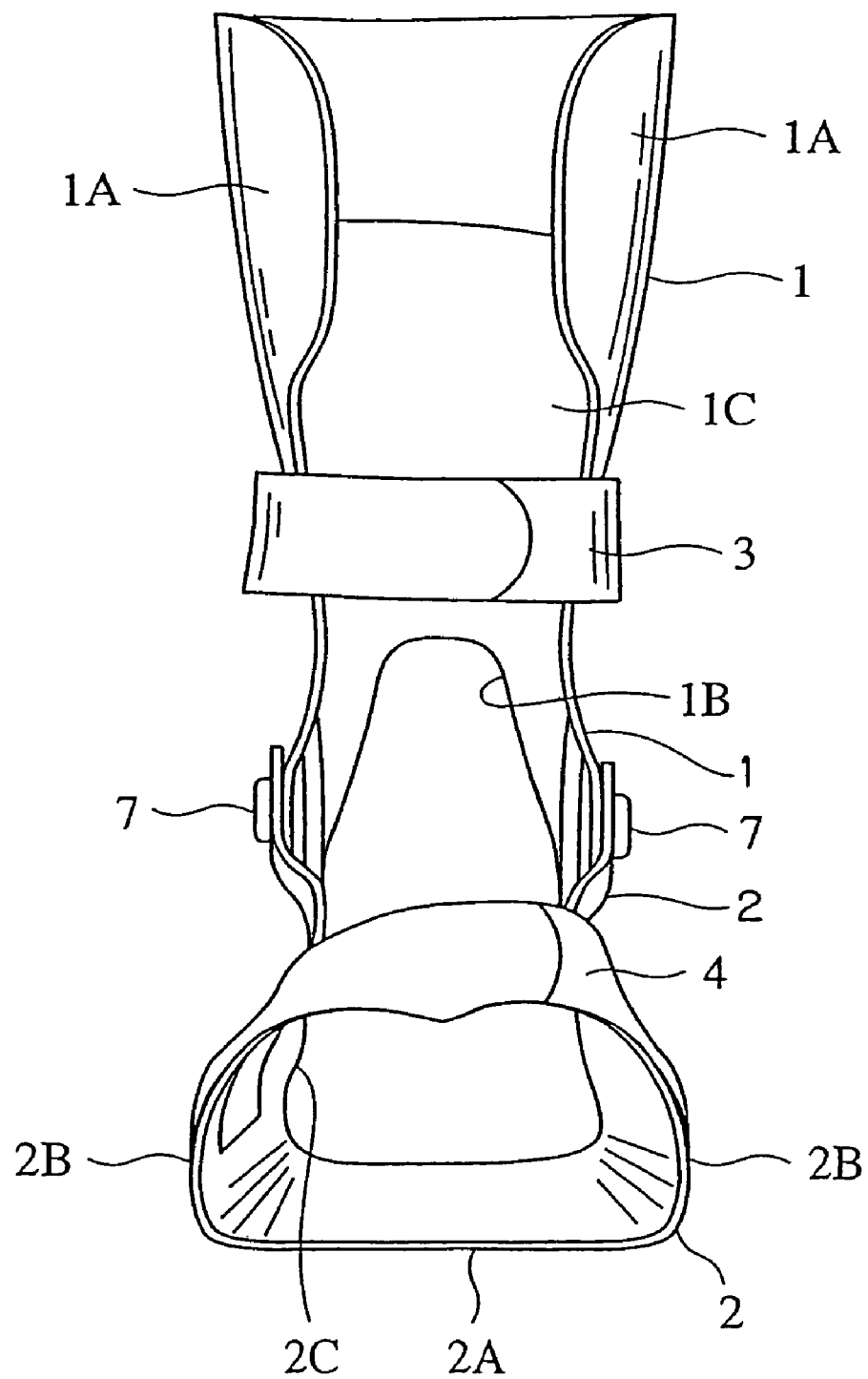
FIG. 3 is a front view of an articulation prosthetic implement using a rotary joint in the first embodiment of the present invention.
Figure 4:
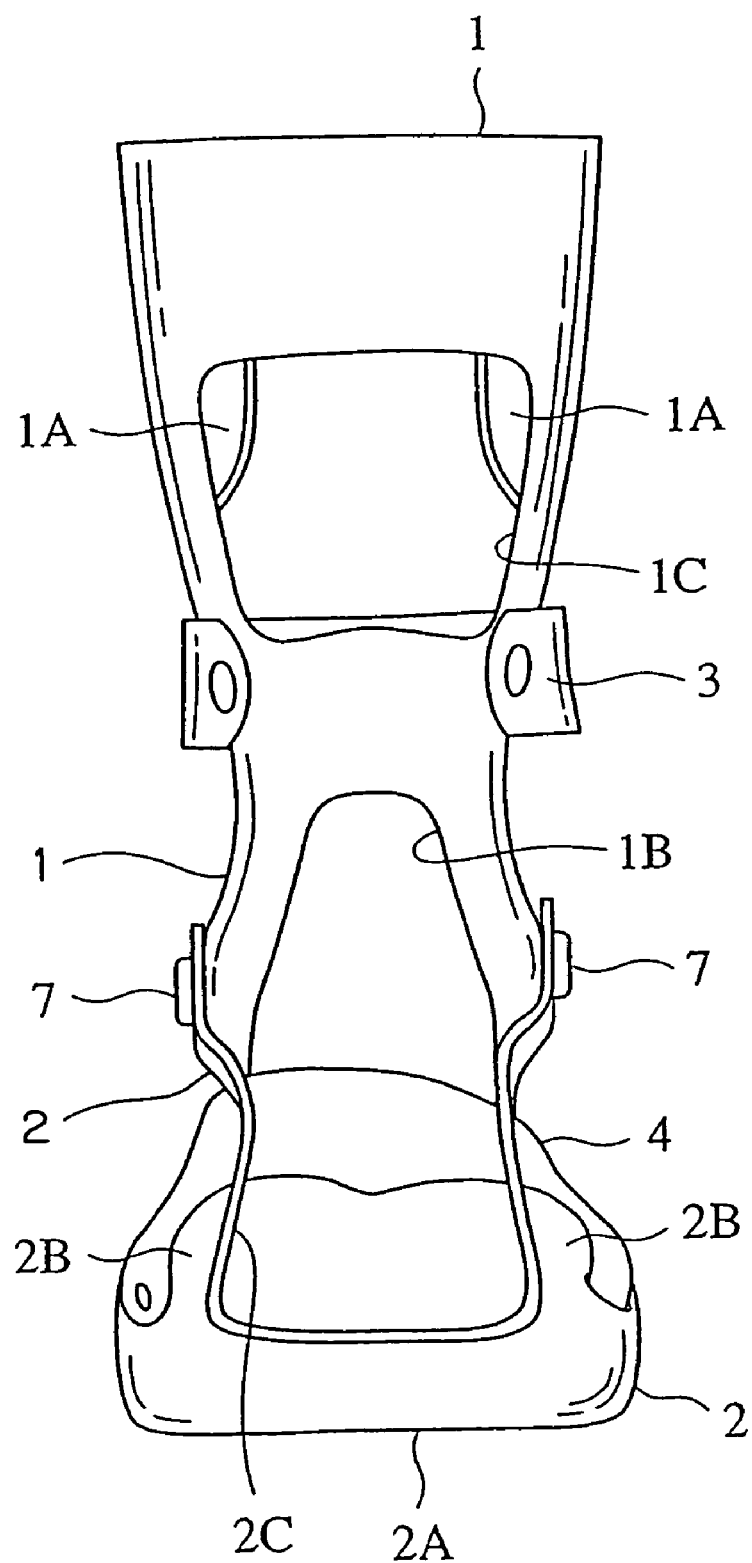
FIG. 4 is a back view of the articulation prosthetic implement shown in FIG. 3.
Figure 5:
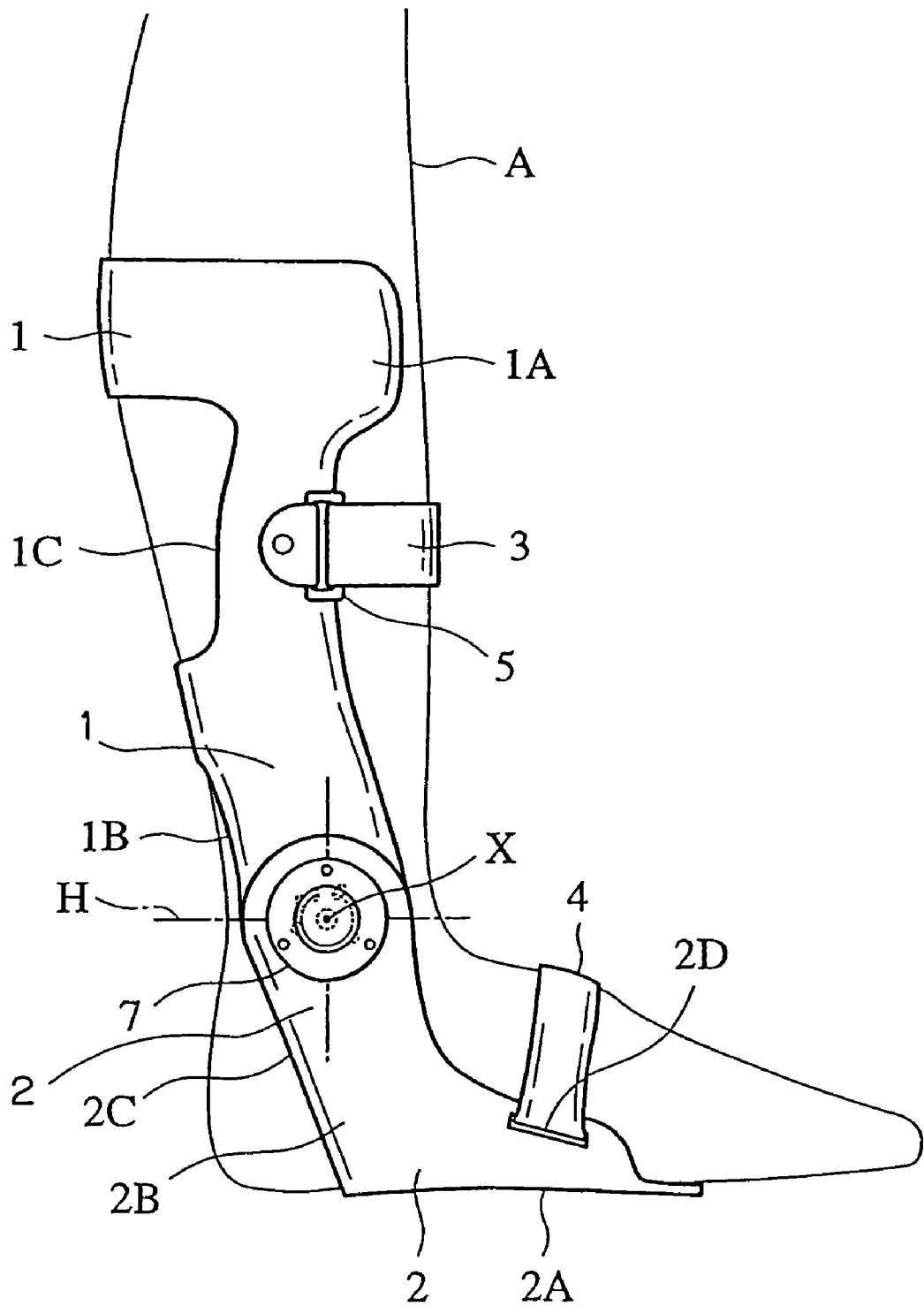
FIG. 5 is a side view of the articulation shown in FIG. 3, FIG. 4 in a state of being fitted to the lower limb.

FIG. 3 to FIG. 5 show an articulation prosthetic implement using a rotary joint in the first embodiment of the present invention shown in FIG. 1. The articulation prosthetic implement comprises lower thigh rear plate (leg protecting plate) 1 provided with a pair of right and left extension parts 1A, 1A which are nearly arcuately curved in plan view for protecting the calf of the leg and protruded forward for partially covering the leg at the upper end side, and two articulation protecting members of foot bottom plate 2 nearly U-shaped in front view which is provided with mount portion 2A having a horizontal surface for placing the foot (below the ankle) thereon and rise portions 2B, 2B rising from the right and left sides of the mount portion 2A, which are main component members, and these vertically adjoining lower thigh rear plate 1 and foot bottom 2 are rotatably connected to each other around the center of horizontal axis. The lower limb below the knee can be fastened to the articulation prosthetic implement by two belts 3, 4 shown in FIG. 3 to FIG. 5. Each of the fixing members, belts 3, 4, has a surface fastener which can be steplessly adjusted with respect to the fastening position, but it is preferable to have a rubber belt, string and the like, or it can be omitted when lower thigh rear plate 1 and foot bottom plate 2 are strong enough to hold the lower limb. One end of one belt 3 is fixed to the front end at one lateral side of lower thigh rear plate 1, and ring-like metal piece 5 (see FIG. 5) for setting the end of belt 3 there through is fixed to the front end at the other lateral side of lower thigh rear plate 1. Also, one end of the other belt 4 is fixed to the upper end at one lateral side of foot bottom plate 2, and hole 2D for setting the end of belt 4 there through is formed in the other upper end at the other lateral side of foot bottom plate 2.

Lower thigh rear plate 1 and foot bottom plate 2 are formed from various types of synthetic resin such as polyethylene or these various types of synthetic resin partially mixed with other substances such as synthetic rubber or metal so as to provide them with flexibility, thereby enabling the reduction of their weights, and they have such advantages that there is no deformation or deterioration due to fatigue in long-time use, and also, twisting loads from the body during walking can be properly absorbed and the original shape can be restored when no load is applied thereto. It is also possible to use materials other than synthetic resin for the configuration.

As shown in FIG. 3, the Achilles' tendon part 1B at the rear end of lower thigh rear plate 1 and heel-bone part 2C at the rear of foot bottom plate 2 are of open type, thereby enabling the reduction in weight of the entire prosthetic implement and making it easier to wear the shoe, and also, it is possible to adjust the flexibility of lower thigh rear plate 1 and foot bottom plate 2. The shoe is omitted in FIG. 3 to FIG. 5. Reference numeral 1C shown in FIG. 3 to FIG. 5 is opening formed nearly in the middle vertically of lower thigh rear plate 1, making it possible to reduce the weight of the entire articulation prosthetic implement. The right and left sides at the lower end of lower thigh rear plate 1 and the right and left sides at the upper end of foot bottom plate 2 are rotatably supported by the rotary joint shown in FIG. 1.

There is provided a rotary joint having a rotating load setting means provided with one-way clutch 50 shown in FIG. 1 to FIG. 3, and thereby, the rotating load against one rotating direction or the direction of back flexion of foot bottom plate 2 can decreased to zero or almost zero, and also, the rotating load against the other rotating direction or the direction of bottom flexion of foot bottom plate 2 can be set to a level high enough to maintain a state just before lifting the foot bottom plate 2 and lower thigh rear plate 1 when foot bottom plate 2 is moved up. In this way, it assures smooth walking. It is preferable to set the rotating load at any levels provided that the level is high enough to maintain a state just before lifting the foot bottom plate 2 and lower thigh rear plate 1 when foot bottom plate 2 is moved up and that it can be rotated so that the bottom surface of foot bottom plate 2 is positioned parallel to or along the ground (surface) due to the load applied from the leg when foot bottom plate 2 is landed.

The rotational center X of lower thigh rear plate 1 is, as shown in FIG. 5, is set to same height with respect to vertical height position H of hominal physiological foot joint axis (also called thigh joint axis), and also, it is set to the position intersecting with the vertical line shown in FIG. 5 or to the position nearly at the center in the forward and backward direction. Thus, setting the rotational center X of lower thigh rear plate 1 as shown is most preferable, but setting it to a slightly deviated position is also preferable.

Figure 6A:
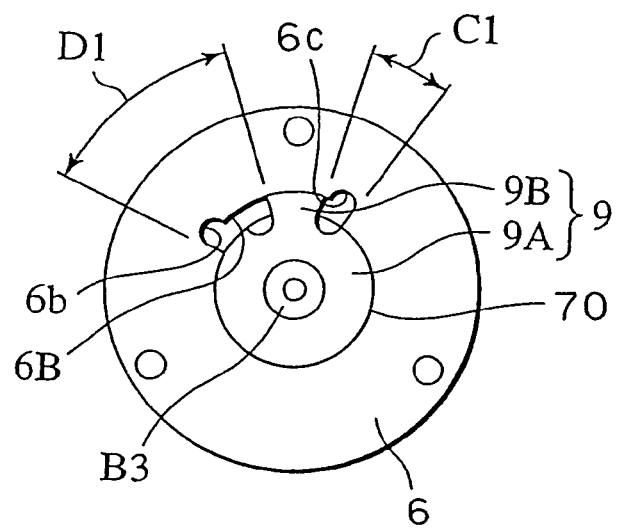
FIG. 6A is a front view showing the relations of a stopper and an inner member.
Figure 6B:
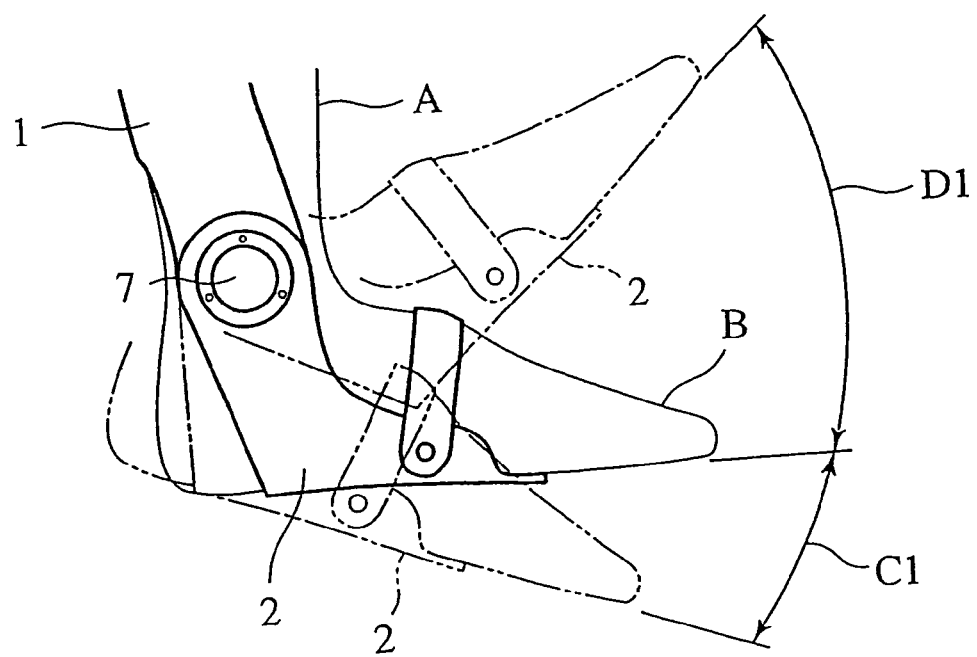
FIG. 6B is an explanatory diagram showing the range of rotation when the one shown in FIG. 6A is used.

The stopper 9 comprises, as shown in FIG. 6A, disk piece 9A for slide-guiding in circular groove 70 of inner member 6 along with the rotation of inner member 6, and projection 9B of nearly trapezoidal in shape protruding partially axially of the outer periphery of disk piece 9A. Also, long groove 6B is formed in the peripheral direction of cylindrical member side edge (axial inner side edge) of flange 6A of inner member 6, and projection 9B is getting into the long groove 6B. Accordingly, foot bottom plate 2 is able to rotate 20 degrees to the bottom flexion side [angle range of C1 shown in FIG. 6A, FIG. 6B] and 45 degrees to the back flexion side [angle range of D1 shown in FIG. 6A, FIG. 6B] from a state of the foot joint set at 0 degree, that is the state (shown by solid line) where foot B and leg A are nearly 90 degrees to each other as shown in FIG. 6B. Notches 6b, 6c arcuately formed toward the axially outer side are formed at both ends of long groove 6B, thereby enabling smooth rotation at both ends even when long groove 6B is not accurately formed up to each end.

Figure 7A:
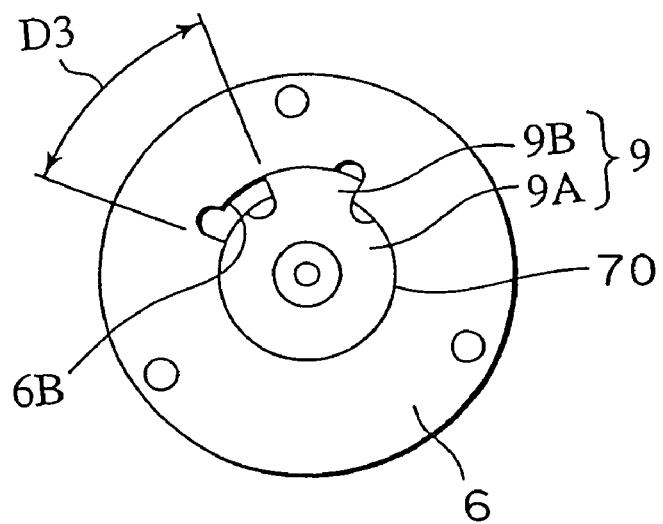
FIG. 7A is a front view showing the relations of a stopper and inner member.
Figure 7B:
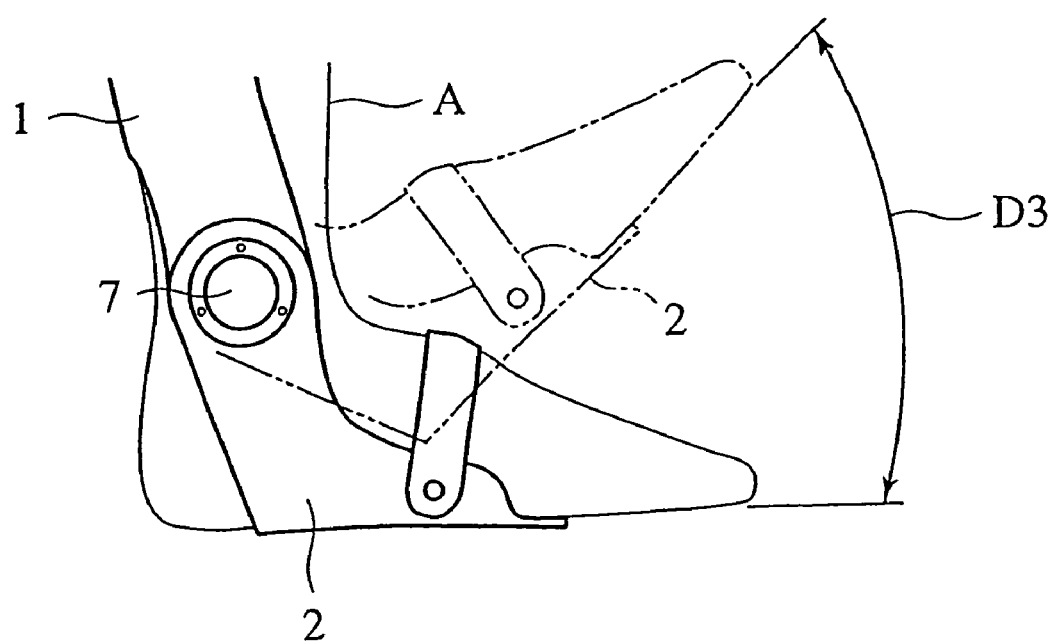
FIG. 7B is an explanatory diagram showing the range of rotation when the one shown in FIG. 7A is used.

Also, as shown in FIG. 7A, the size (width size) in the peripheral direction of projection 9B of stopper 9 is larger (wider) than stopper 9 shown in FIG. 6A, and foot bottomplate 2 is able to rotate 45 degrees [angle range of D3 shown in FIG. 2A, FIG. 7B] only to the back flexion side from a state of the foot joint set at 0 degree as described above. Thus, it is possible to properly change the length of long groove 6B and the width of projection 9B.

The movable range of a human leg joint is less than 45 degrees with respect to both of bottom flexion and back flexion (sometimes less than 35 degrees), and by setting the rotational angle to 45 degrees as described above, it is possible to obtain a state equivalent to being free without limitation on angle for a human body. Also, it is sometimes necessary to change the limitation on angle according to the degree (level) of the symptom of clubfoot, but there is no problem even when executed in a completely free state with stopper 9 omitted.

Described in the following is the case of walking with an articulation prosthetic implement configured as described above fitted to an affected part. First, in walking on a flat road where the ground is horizontal, as shown in FIG. 8A, when the normal left foot is moved a step forward from a state with the normal left foot and the right foot on the prosthetic implement arranged in order as viewed from side, the right leg A at the implement side is inclined 15 degrees [angle of E1 in FIG. 8B] from its vertical position, as shown in FIG. 8B. In this case, since the rotating load to the back flexion side is zero or almost zero, lower thigh rear plate 1 is able to smoothly rotate to the angle of leg A. Subsequently, when the right foot on the prosthetic implement is raised from the ground to move a step forward, then as shown in FIG. 8C, the right foot can be moved while maintaining the position (with the right leg A inclined 15 degrees forward from the vertical position) just before raising, and the right foot tip will not droop forward to touch the ground. And, when the right foot heel is landed on the ground, foot bottom plate 2 rotates 15 degrees [angle of E2 in FIG. 8D] to the bottom flexion side due to the load then applied, and the position is changed so that the bottom surface of foot bottom plate 2 is paralleled with the ground surface.

Figure 9A:
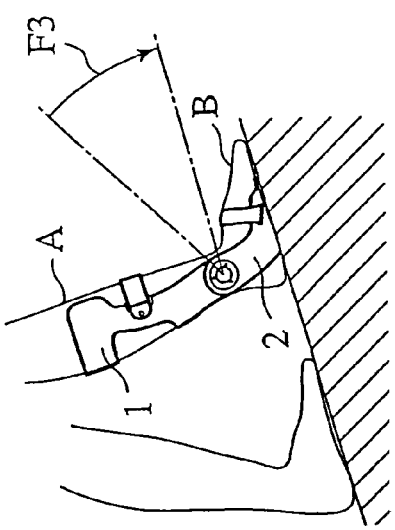
FIG. 9A shows a state of walking with the feet arranged in order.
Figure 9B:
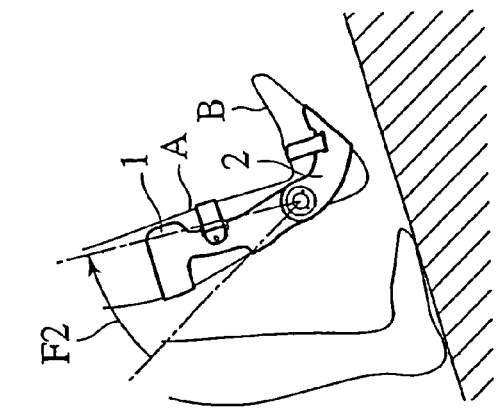
FIG. 9B shows a state of walking with the left foot moved a step forward.
Figure 9C:
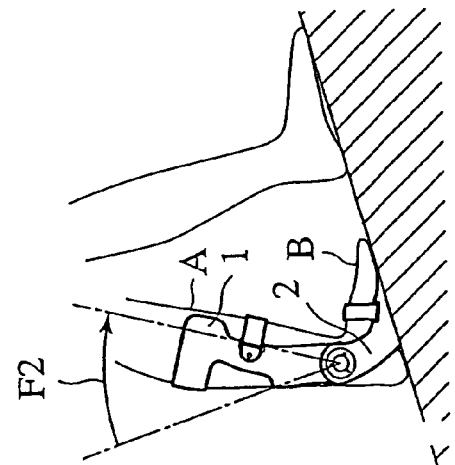
FIG. 9C shows a state of walking just before landing with the right foot stepped forward.
Figure 9D:
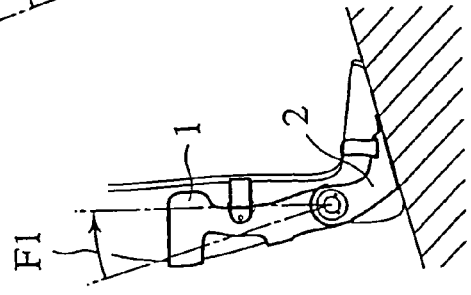
FIG. 9D shows a state of walking with the right foot stepped forward and landed.

Described next is the case of walking on an upward slope (ascent). As shown in FIG. 9A, when the normal left foot is moved a step forward from a state with the normal left foot and the right foot on the prosthetic implement arranged in order as viewed from side or more in detail from a position with the leg inclined 15 degrees forward [angle of F1 in FIG. 9A] to any foot from the vertical position, the right leg A at the implement side is inclined 15 degrees more from the position inclined forward to take a position inclined 30 degrees forward [angle of F2 in FIG. 9B], as shown in FIG. 9B. In this case, since the rotating load to the back flexion side is zero or almost zero, the lower thigh rear plate 1 is able to smoothly rotate to match the angle of leg A. Subsequently, when the right foot on the prosthetic implement is raised from the ground to move a step forward, then as shown in FIG. 9C, the right foot can be moved while maintaining the position (with the right leg A, inclined 30 degrees forward) just before raising, and the right foot tip will not droop forward to touch the ground. And, when the right foot heel is landed on the ground, foot bottom plate 2 rotates 30 degrees [angle of F3 in FIG. 9D] to the bottom flexion side due to the load then applied, and the position is changed so that the bottom surface of foot bottom plate 2 is paralleled with the ground surface.

Figure 10A:
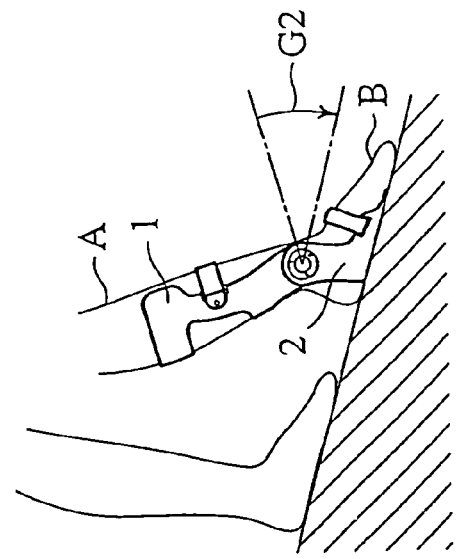
FIG. 10A shows a state of walking with the feet arranged in order.
Figure 10B:
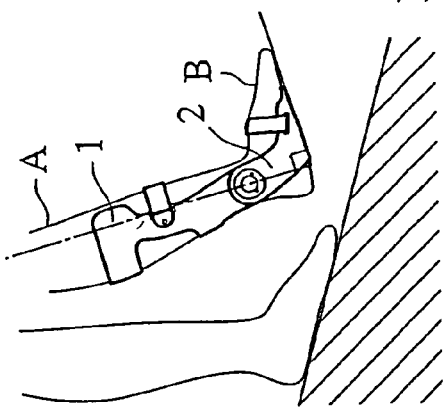
FIG. 10B shows a state of walking with the left foot moved a step forward.
Figure 10C:
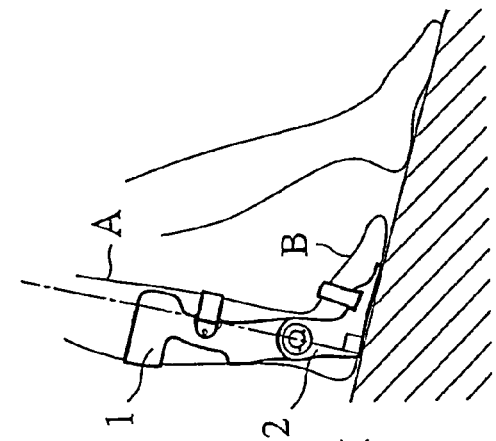
FIG. 10C shows a state of walking just before landing with the right foot stepped forward.
Figure 10D:
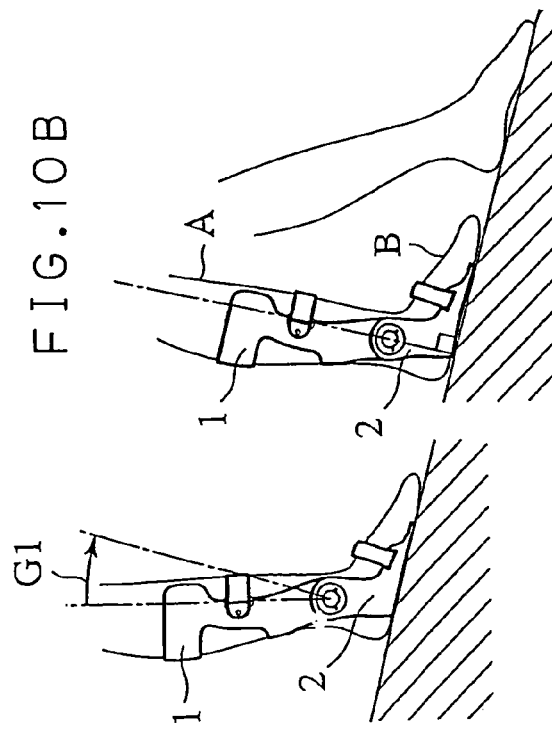
FIG. 10D shows a state of walking with the right foot stepped forward and landed.

Finally described is the case of walking on a downward slope. As shown in FIG. 10A, when the normal left foot is moved a step forward from a state with the normal left foot and the right foot on the prosthetic implement arranged in order as viewed from side or more in detail from a position with the leg inclined 15 degrees backward [angle of G1 in FIG. 10A] to any foot from the vertical position, the right leg A at the implement side is inclined forward from the position inclined backward to take a position vertical to the ground, as shown in FIG. 10B. In this case, since the rotating load to the back flexion side is zero or almost zero, the lower thigh rear plate 1 is able to smoothly rotate to match the angle of leg A. Subsequently, when the right foot on the prosthetic implement is raised from the ground to move a step forward, then as shown in FIG. 10C, the left foot can be moved while maintaining the position (with the right leg A vertical to the ground) just before raising, and the right foot tip will not droop forward to touch the ground. And, when the right foot heel is landed on the ground, foot bottom plate 2 rotates 30 degrees [angle of G2 in FIG. 10D] to the bottom flexion side due to the load then applied, and the position is changed so that the bottom surface of foot bottom plate 2 is paralleled with the ground surface.

Figure 11:
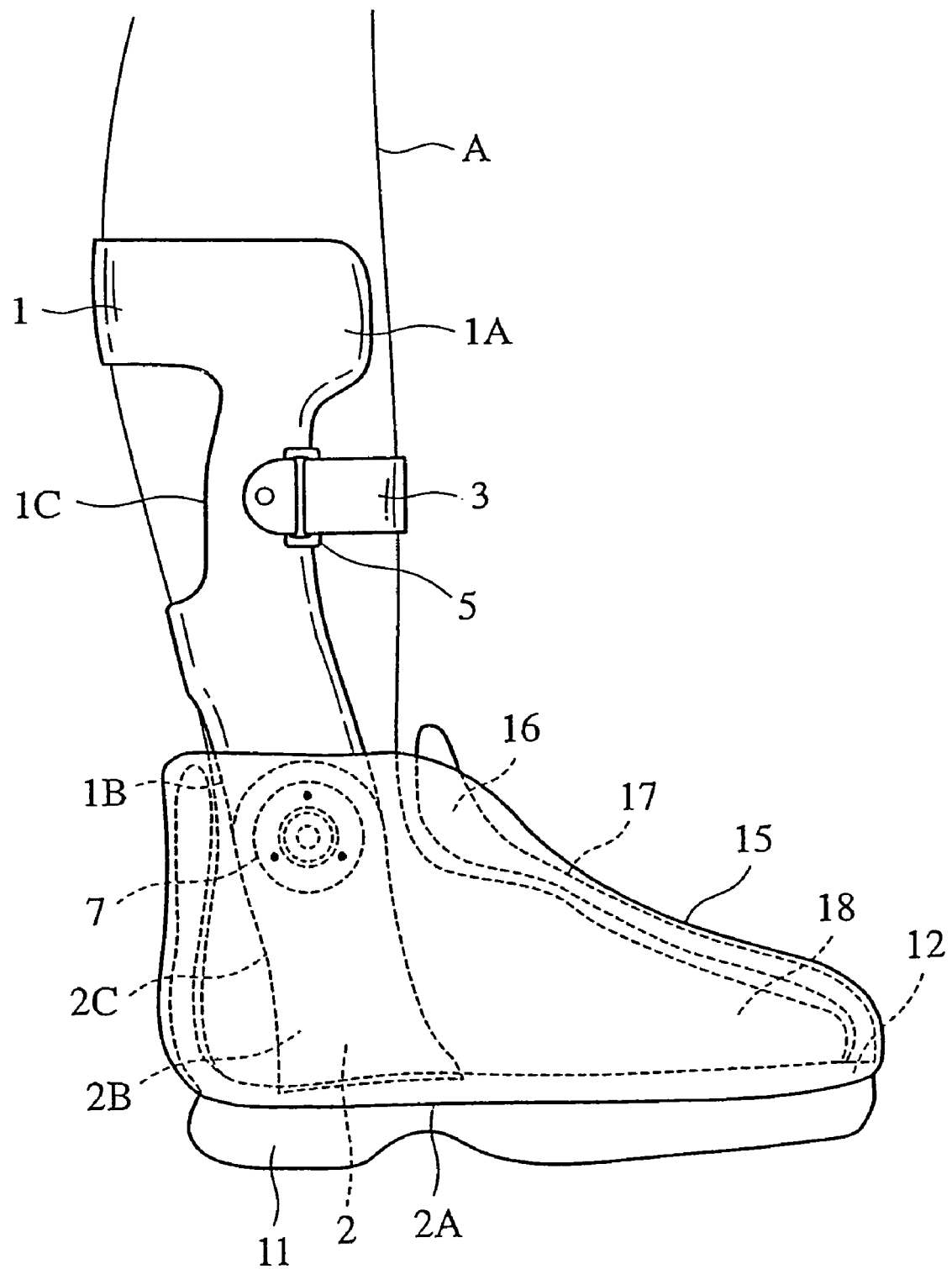
FIG. 11 is a side view of an articulation prosthetic implement in a moderation example of the first embodiment of the present invention.
Figure 12:
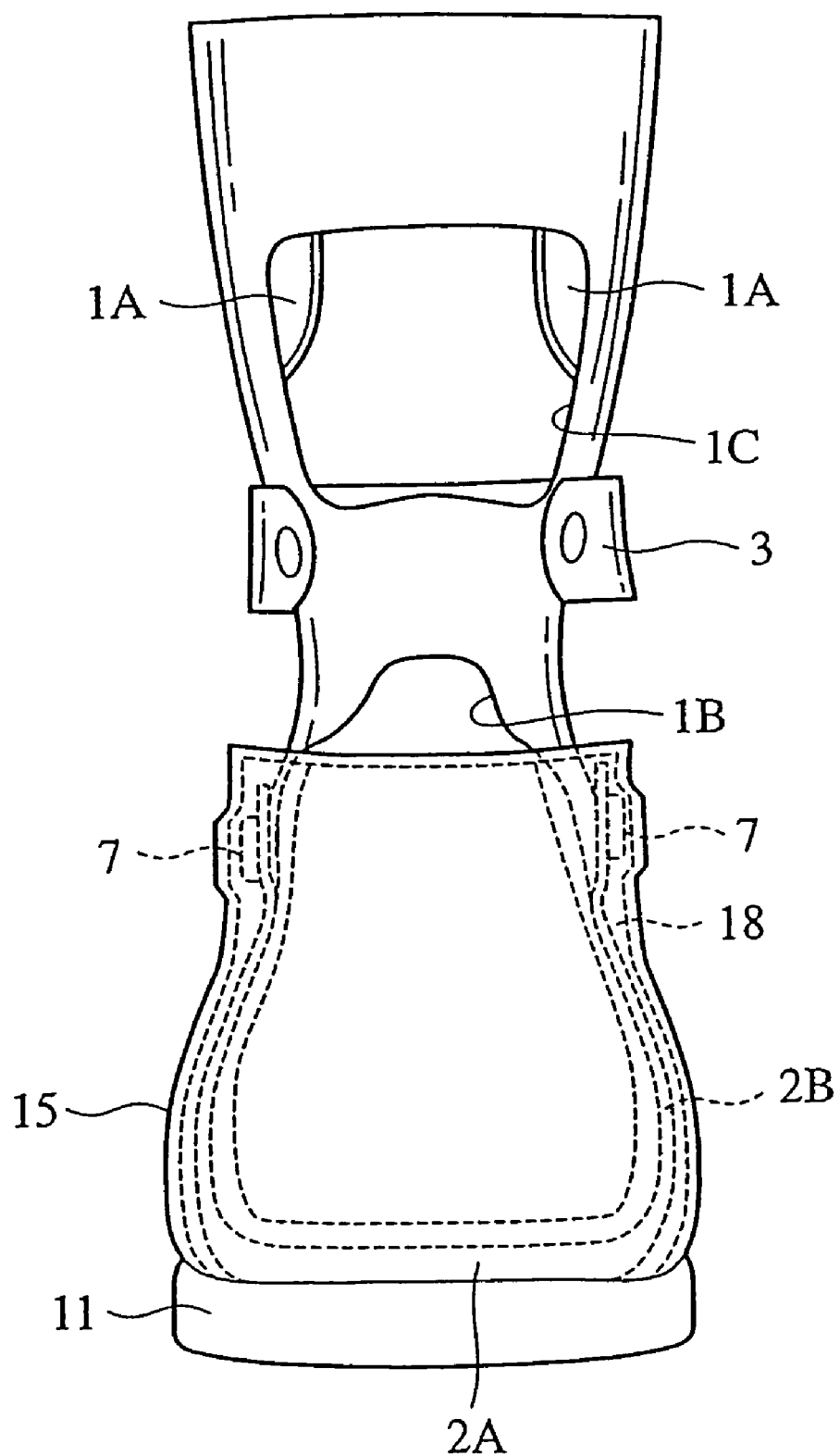
FIG. 12 is a back view of an articulation prosthetic implement in a moderation example of the first embodiment of the present invention.

FIG. 11 is a side view of an articulation prosthetic implement in a moderation example of the first embodiment, and FIG. 12 is a back view of the same. In this moderation example, in the first embodiment, the portion below outer member 7 is provided one-piece with shoe 15.

In this moderation example, belt 4 that is the fixing member shown in FIG. 3 to FIG. 5 is omitted since the foot is secured by front leather part 17 and tongue leather part 16 of shoe 15. Also, it is preferable to provide front leather part 17 with a string or flexible rubber in order to secure the instep. Also, rise portion 2B is previously provided along inner portion 18 in the shoe. Similarly, mount portion 2A is integral with inner bottom 12 in the shoe or sole 11. In this case, the mount portion can be fixed with screw or the like.

The other parts are substantially same as in the first embodiment, and the description is omitted. In this moderation example, the portion formed one-piece with the shoe is a portion generally below the calf, but it is preferable to properly adjust the shape of extension part 1A or lower thigh rear plate 1 in accordance with the type and use of the shoe. Also, it is preferable to provide an opening for adjustment in the shoe for the purpose of adjusting the rotating load adjusting means.

When the person wears a shoe after installing the first embodiment, since the shoe is tight for the thickness of heelbone part 2C and mount portion 2A, and in addition, the shoe is separate from the prosthetic implement, it causes inconvenience in taking exercise. In this moderation example, since the extension part and the mount portion are stored in the shoe, it will lessen the sense of incongruity when taking exercise or the like. Also, outer member 7 is stored in the shoe, and it will bring about an advantage that the connections are protected.

Figure 13:
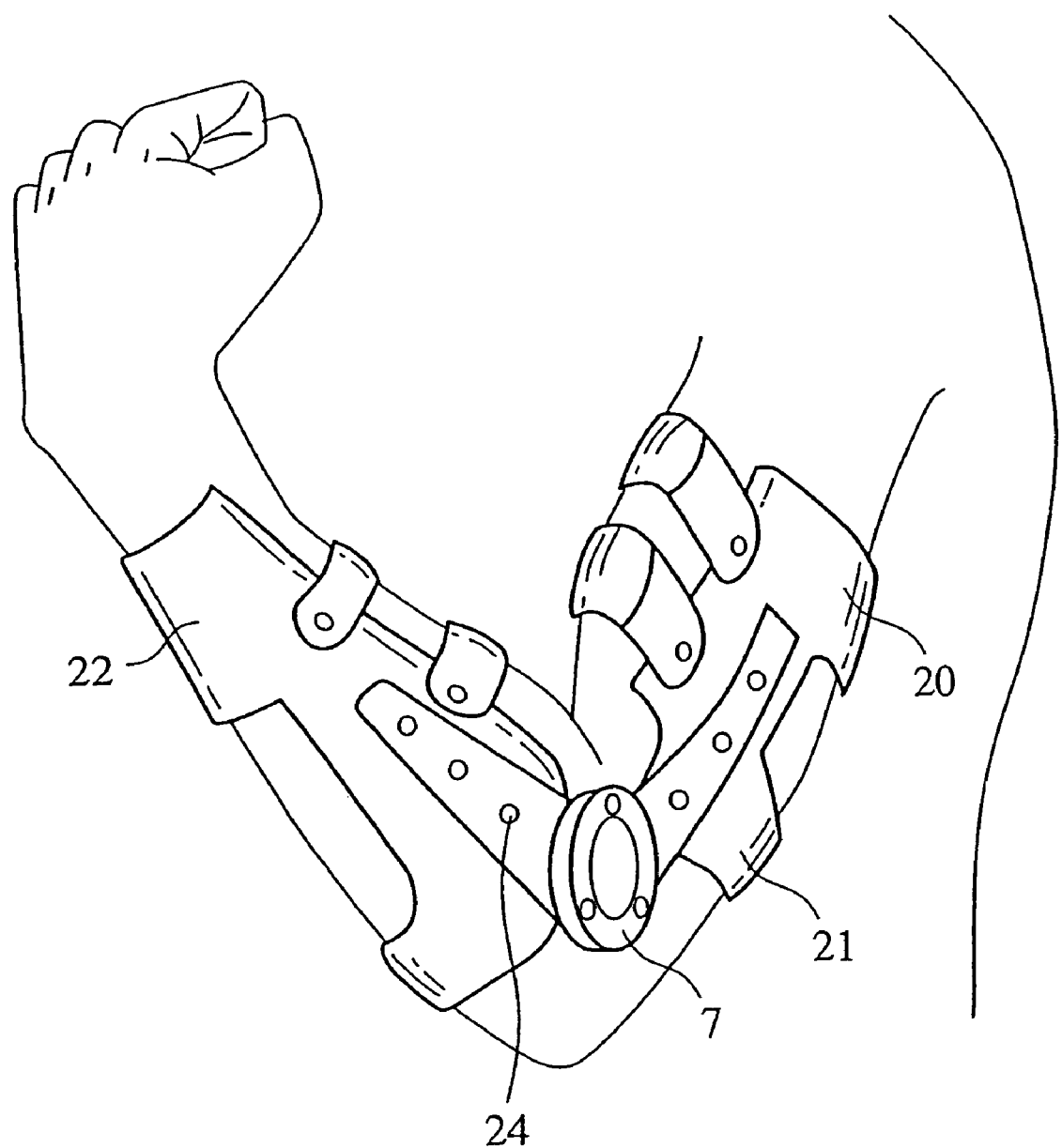
FIG. 13 is a perspective view showing a state of an articulation prosthetic implement fitted to an arm in the second embodiment of the present invention.
Figure 14A:
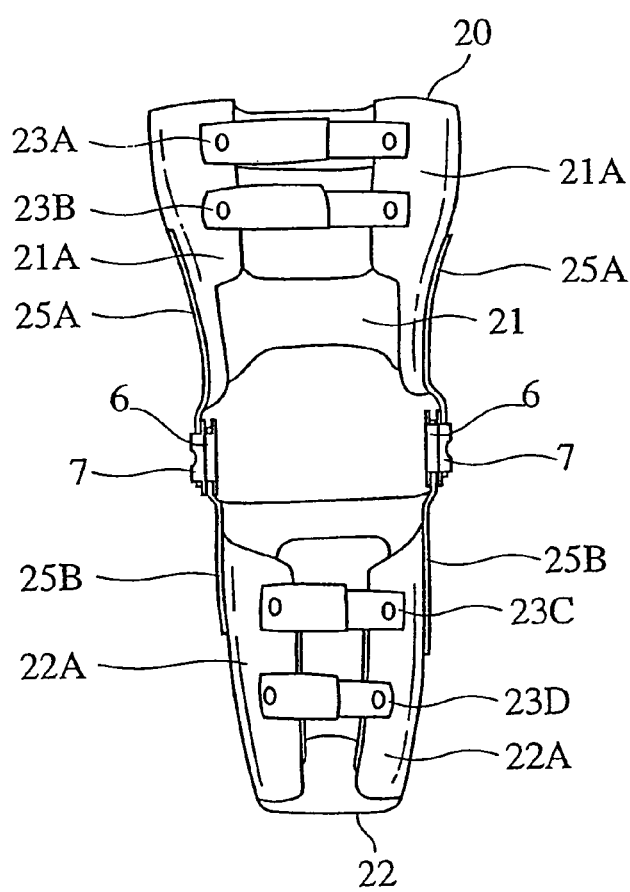
FIG. 14A is a front view of the implement.
Figure 14B:
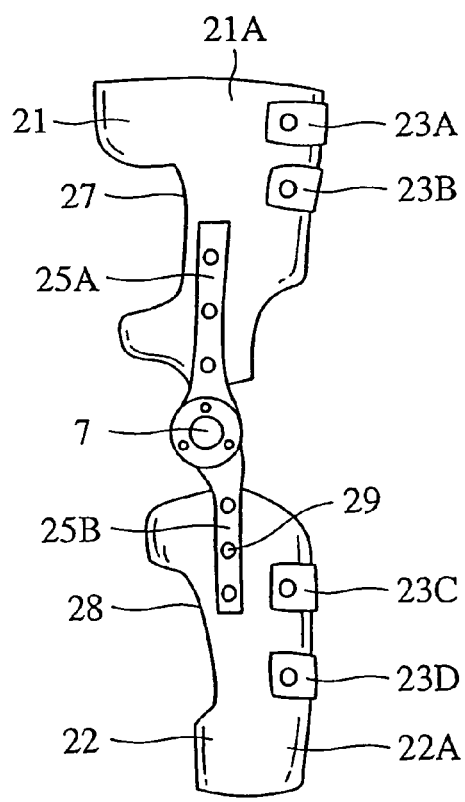
FIG. 14B is a side view of the implement.

FIG. 13, FIG. 14A and FIG. 14B show an articulation prosthetic implement in the second embodiment of the present invention.

Articulation prosthetic implement 20 comprises plate 21 having a pair of right and left extension parts 21A, 21A for protecting the rear of the upper arm, and forearm plate 22 having a pair of right and left extension parts 22A, 22A similarly for protecting the rear of the forearm, which is arcuately curved. These upper arm and forearm plates 21, 22 are rotatably connected to each other about the center of the horizontal axis nearly from the elbow cell to the elbow. In this case, the outer member 7 and the inner member 6 are connected by connection member 25A for upper arm plate 21 and connection member 25B for forearm plate 22. And, the two connection members 25A, 25B are secured by screw 29 to plates 21, 22, respectively.

Also, the upper arm and forearm can be fastened to the prosthetic implement 20 by means of four belts 23A to 23D disposed in the prosthetic implement 20. The fixing members, belts 23A to 23D can be steplessly adjusted with respect to the fastening position the same as for fixing belts 3, 4 described in the first embodiment. The number of fixing members is not always necessary to be four, and it is preferable to have a rubber belt, string and the like provided that prosthetic implement 20 can be fixed. It is also preferable to use metal piece 5 or the like although it is not shown in the figure.

Also, plates 21, 22 for the upper arm and the forearm are respectively provided with openings 27, 28 nearly at the back of the upper arm and the back portion of the forearm, thereby realizing the weight reduction. The other parts are substantially same as in the first embodiment, and the description is omitted.

Prosthetic implement 20 of this embodiment realizes a prosthetic implement suited for the user because the load setting can be properly adjusted unlike a plaster cast or the like which simply fixes the arm.

Figure 15:
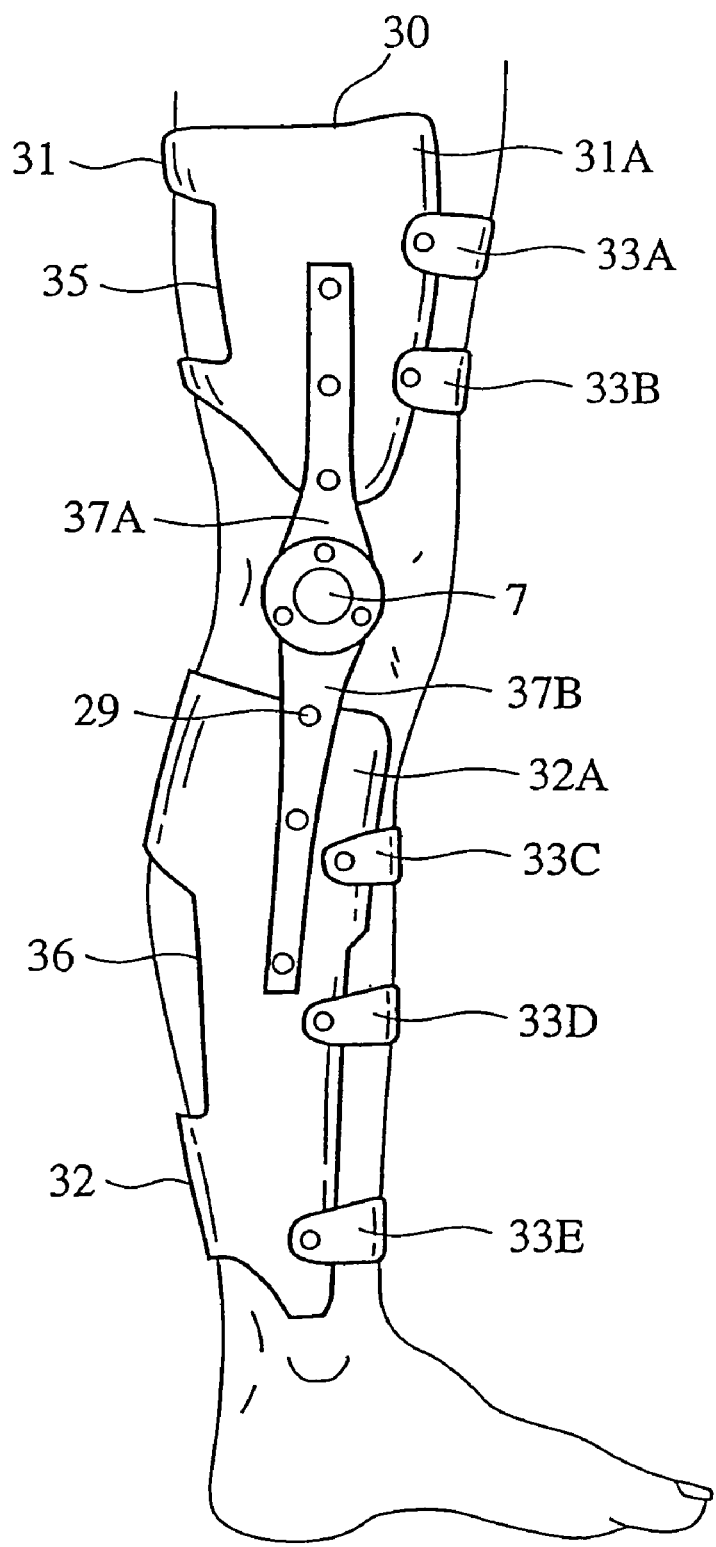
FIG. 15 is a side view showing a state of an articulation prosthetic implement fitted to a leg in the third embodiment of the present invention.
Figure 16:
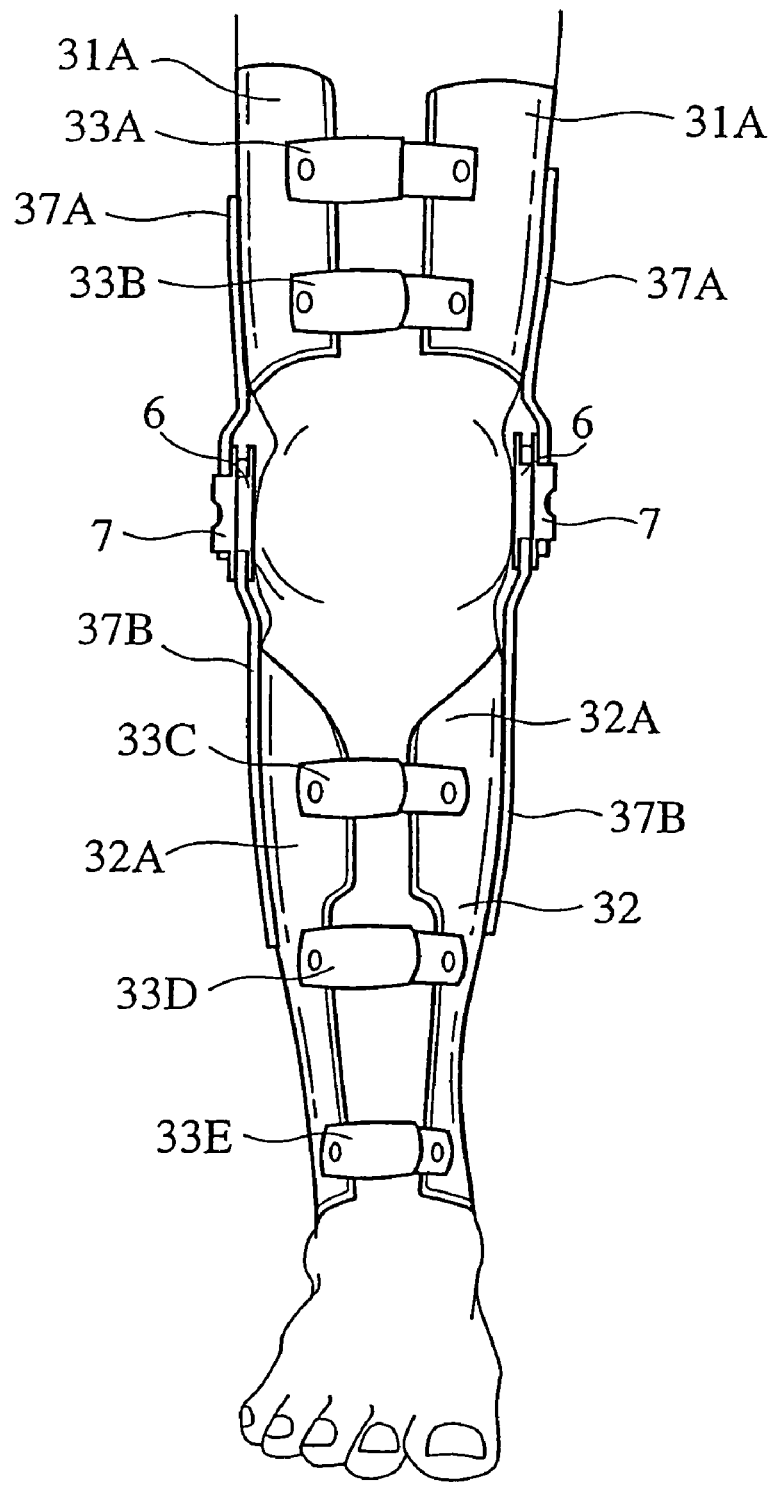
FIG. 16 is a front view of the articulation prosthetic implement shown in FIG. 15.
Figure 17:
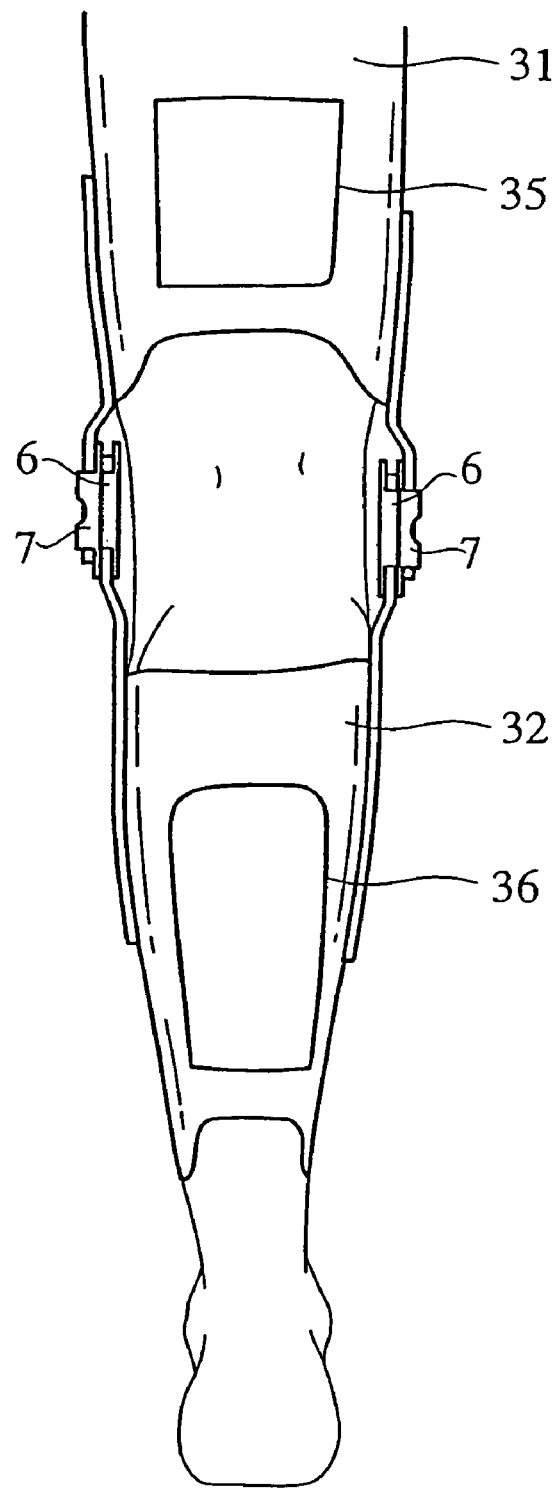
FIG. 17 is a back view of the articulation prosthetic implement shown in FIG. 15.

FIG. 15 to FIG. 18 show an articulation prosthetic implement in the third embodiment of the present invention. FIG. 15 is a side view of prosthetic implement 30 of this embodiment. Prosthetic implement 30 comprises thigh plate 31 having a pair of right and left extension parts 31A, 31A for protecting the rear of the thigh, and lower thigh plate 32 having a pair of right and left extension parts 32A, 32A similarly for protecting the rear of the thigh, which are arcuately curved. These lower thigh and thigh plates 31, 32 are rotatably connected to each other about the center of the horizontal axis nearly from. the knee cell to the knee. In this case, the outer member 7 and the inner member 6 are connected by connection member 37A for thigh plate 31 and connection member 37B for lower thigh plate 32. And, the two connection members 37A, 37B are secured by screw 29 to plates 31, 32, respectively. Also, the lower thigh and the thigh can be fastened to prosthetic implement 30 by means of five belts 33A to 33E disposed in the prosthetic implement 30. Also, the adjustment can be made by using metal piece 5 or the like although it is not shown in the figure. Plates 31, 32 for the thigh and the lower thigh are respectively provided with openings 35, 36 nearly at the back of the thigh and around the calf, thereby realizing the weight reduction.

Figure 18:
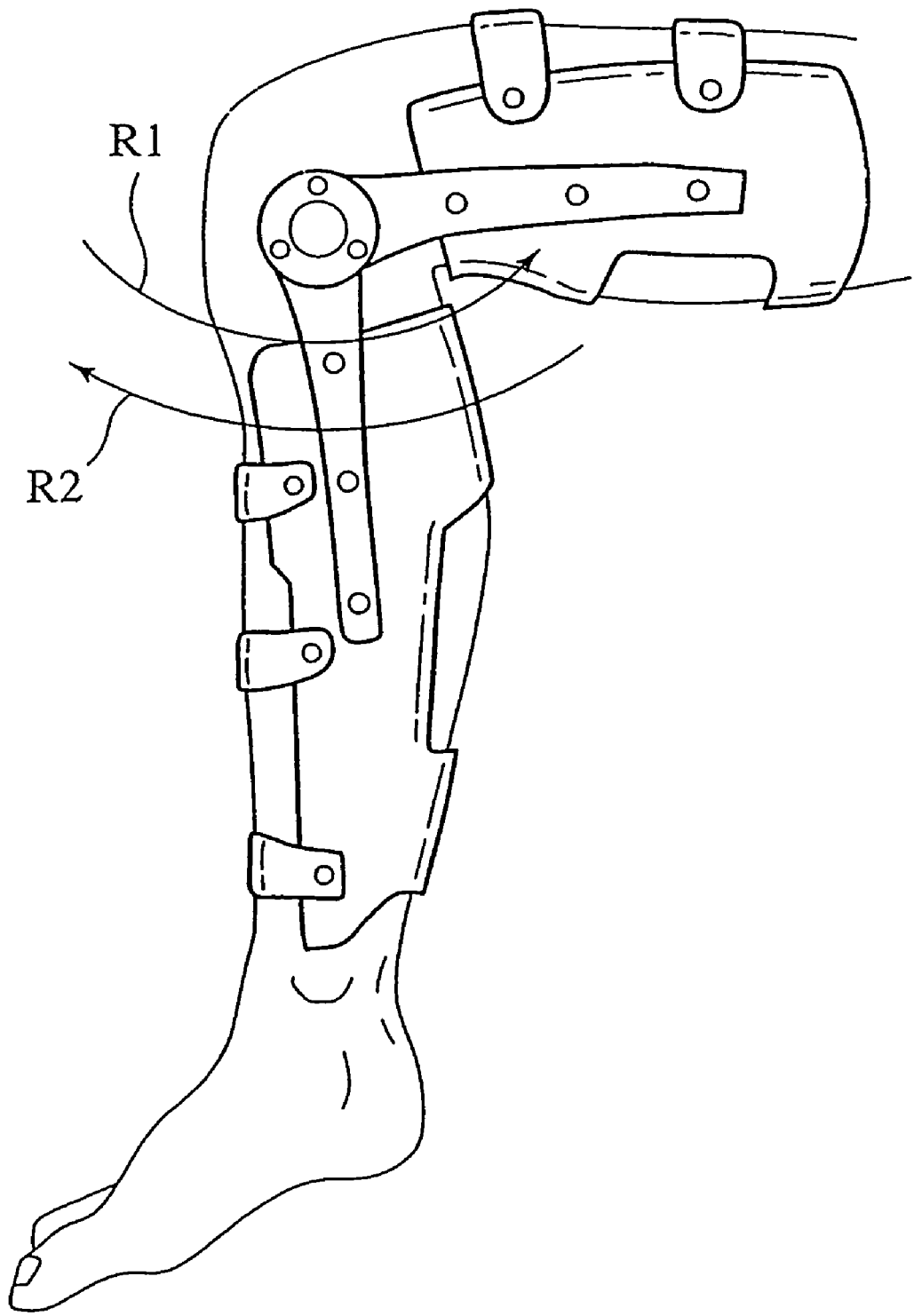
FIG. 18 is a diagram showing the load setting in the articulation prosthetic implement shown in FIG. 15.
Figure 19:
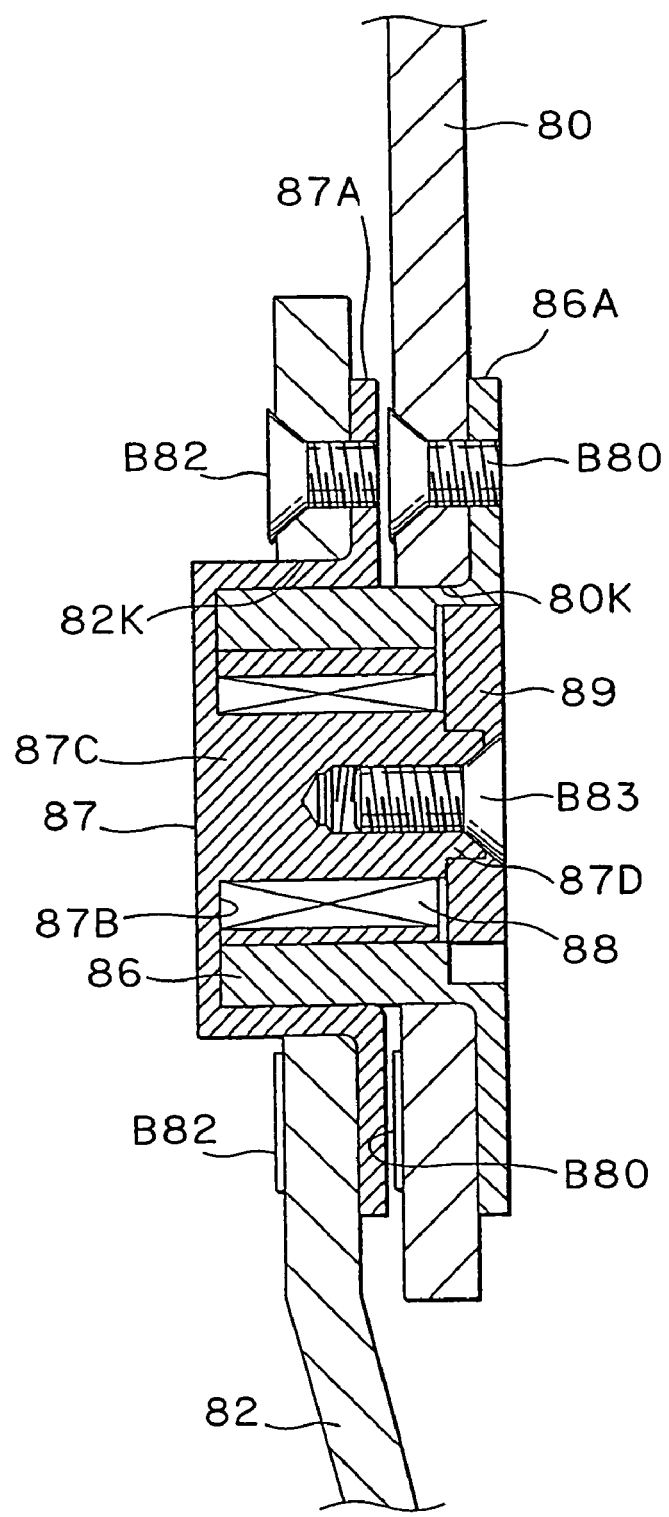
FIG. 19 is a sectional view around a rotary joint of a conventional articulation prosthetic implement having a rotating load setting means.

For example, in prosthetic implement 30 as shown in FIG. 18, when the knee flexes in one rotating direction R1, it is set so that the rotating load is nearly zero, and when it flexes in the other rotating direction R2, it is set so that the rotating load is greater than the load in direction R1. According to the setting, for example, when walking up the steps, with the foot at the normal side used as a support, the foot on prosthetic implement 30 at the opposite side is raised, then. the load in direction R1 is zero, and therefore, the knee can be naturally flexed enough to go up the steps as the thigh flexes. Subsequently, until the foot on prosthetic implement 30 reaches the next step according to the movement of weight supported by the foot at the normal side, the angle of the knee can be maintained at the position since the load in rotating direction R2 is set greater. After the movement of weight, the foot wearing the prosthetic implement 30 reaches the surface of the step, then the prosthetic implement 30 is rotated by a part of the load applied to the knee.

By using prosthetic implement 30 of the third embodiment as described above, even when the load applied to one knee as in going up the steps is greater than that applied thereto in walking on a flat road, it is possible to realize a prosthetic implement which may support the walk and absorb the shocks.

Also, it is preferable to put the embodiment 1 on the ankle and to use the third embodiment 3 on. the knee. The other parts are substantially same as in the first embodiment, and the description is omitted.

Also, the prosthetic implement of the present invention can be applied to a joint connection for a wrist, shoulder and the like besides the above example, and it is possible to properly change the shape of the prosthetic implement and the specific configuration.

The manufacturing (assembling) method for the articulation prosthetic implement of the present invention will be described in the following with respect to the embodiment shown in FIG. 1 to FIG. 5. Previously manufactured is the one with one-way clutch 50 covered and fitted with metal bush 52, the metal bush 52 covered and fitted with synthetic resin bush 54, and the synthetic resin bush 54 covered and fitted with brake bush 56. And, there are provided rotary shaft 7C at the inner side and annular depression 7B around the rotary shaft, and after covering and fitting the rotary shaft 7C of outer member 7 having flanges 7A at either end with one-way clutch 50 having three bushes 52, 54, 56, the cylindrical projection 58 of inner member 6 having flanges 6A at either end is fitted in the annular depression 7B of the outer member located outside the brake bush 56. Subsequently, stopper 9 for controlling the range of rotation of the rotary shaft is screwed or bolted to inner projection 7D of rotary shaft 7C.

Thus, after assembling the rotary joint having a rotating load setting means, lower thigh rear plate 1 that is one articulation protecting member of the articulation prosthetic implement is fitted to flange 6A of inner member 6 from the surface side (right-hand side in FIG. 1) of the inner member, and foot bottom plate 2 that is the other articulation protecting member of the articulation prosthetic implement is fitted to flange 7A of outer member 7 from the surface side (left-hand side in FIG. 1) of the outer member. Reference numeral 1K is a groove for fitting the lower end opening of lower thigh rear plate 1 therein, and numeral 2K is a groove for fitting the upper end opening of foot bottom plate 2 therein.

In the present invention, since the single unit of a rotary joint can be previously assembled and completed, it is possible to easily execute the tests such as a torque test with a rotary joint unit and to stabilize the load, thereby improving the assembling method and the working efficiency. Also, as an independent product in the form of a rotary joint unit, it enables the manufacture of special items.

Also, according to the present invention, setting the rotating load to the bottom flexion side greater than the rotating load to the back flexion side, when raising the landed foot, it can be maintained by the articulation prosthetic implement to the angle of the foot just before raising, and therefore, the foot tip will not droop downward to touch the ground simultaneously when the foot is raised, and also, it can be easily and smoothly turned to the back flexion side. Also, since the load of a part of weight applied with the foot landed is converted into a rotating force for rotating the articulation protecting member, even when the rotating load is set greater, it is possible to smoothly rotate the articulation protecting member to execute bottom flexion that used to be impossible. Accordingly, it is possible to provide an articulation prosthetic implement which enables almost natural walking while making smooth bottom flexion and back flexion in any places (varying road conditions) as in walking on slopes (upward and downward), waking from a flat road to a slope or from a slope to a flat road as well as walking on a flat road.

Also, according to the present invention, setting the rotating load to a level such that the load applied with the foot bottom plate landed causes the foot bottom plate to be rotated and paralleled with the ground surface, and the state just before raising the foot bottom plate and the leg protecting plate can be maintained, it is possible to avoid stumbling due to the foot touching the slope when the foot is raised, and also, when the foot bottom plate is landed, the load (a part of weight) applied with the foot landed causes the foot bottom plate to smoothly rotate, and thereby, it is possible to make an articulation prosthetic implement which is easier to handle.

Also, according to the present invention, since the heelbone part at the rear of the foot bottom plate and the Achilles' tendon part at the lower end rear of the lower thigh rear; plate which are free from problems with respect to strength are of open type; it is possible to reduce the weight and to make easier to wear a shoe. Also, the flexibility of the foot bottom plate and the lower thigh rear plate can be adjusted, and it is possible to configure an articulation prosthetic implement suited for patents.

Also, according to the present invention, setting the rotational center of the lower thigh rear plate to a height nearly the same as the vertical height position of hominal physiological foot joint axis, the rotational center of the foot joint axis and lower thigh rear plate can be made nearly equal to the rotational center of the foot bottom plate, and it is possible to configure an articulation prosthetic implement which allows the foot joint axis of a human body to move easily and is easier to handle.

Also, according to the present invention, since an opening is formed in a vertical middle portion of the lower thigh rear plate, the weight can be further reduced, and also, the flexibility can be improved, and it is possible to configure an articulation prosthetic implement most suited for any patents.

Also, according to the present invention, since there is provided a fixing member for fixing a human body to the lower thigh rear plate or the foot bottom plate over the right and left front ends of the lower thigh rear plate or the right and left upper ends of the foot bottom plate, it is possible to avoid removal of the articulation prosthetic implement during walking, thereby bringing about an advantage such that smooth walking is realized.

Also, according to the present invention, since the rotating load setting means is configured with a one-way clutch and bush disposed on the rotary shaft of the articulation protecting member, the rotating load to one side (e.g. to the back flexion side) can be eliminated as much as possible, and the rotating load to the other side (e.g. to the bottom flexion side) can be set to a level such that the foot bottom plate is not rotated by the weight of the foot placed on the foot bottom plate, and thereby, it is possible to assure further natural (smooth) walking.

Also, according to the present invention, since the rotating load to one side (e.g. to the back flexion side) can be eliminated as much as possible, and the rotating load to the other side (e.g. to the bottom flexion side) can be set to a level such that the foot bottom plate is not rotated by the weight of the foot placed on the foot bottom plate, and thereby, it is possible to provide an articulation prosthetic implement which may assure further natural walking without limitations on bottom flexion and back flexion.

Also, it is preferable to use a configuration with this invention installed in a shoe. Since the mount portion and the like are housed in the shoe, it is possible to provide an articulation prosthetic implement which may stand use for taking exercise or the like.

Also, according to the present invention, it is possible to configure a prosthetic implement with the protecting plates for upper arm and forearm connected to each other by the rotating load setting means. In this configuration, setting one rotating load greater than the other rotating load, it is possible to provide a prosthetic implement for the elbow according to the condition of the user.

Also, according to the present invention, it is possible to configure an articulation prosthetic implement with the protective plates for the thigh and the lower thigh connected to each other by the rotating load setting means. In this configuration, setting one rotating load greater than the other rotating load, it is possible to provide a prosthetic implement for the knee which may properly compensate for the flexion of the knee in going up and down the steps or the like and prevent accidents such as stumbling.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A manufacturing method for an articulation prosthetic implement having a rotating load setting means, comprising the steps of previously manufacturing a one-way clutch covered and fitted with a metal bush, the metal bush covered and fitted with a synthetic resin bush, and the synthetic resin bush covered and fitted with a brake bush, and covering and fitting a rotary shaft of an outer member with flanges at either end, having a rotary shaft at the inner side and an annular depression around the rotary shaft, with the one way clutch having the three bushes, followed by fitting a cylindrical projection of an inner member having flanges at either end into the annular depression of the outer member located outside the brake bush, subsequently screwing or bolting a stopper for controlling the range of rotary shaft rotation to an inner projection of the rotary shaft, fitting one articulation protecting member of the articulation prosthetic implement to the flange of the inner member from the surface side of the inner member, and fitting the other articulation protecting member of the articulation prosthetic implement to the flange of the outer member from the surface side of the outer member.

* * * * *